(12) United States Patent
Weakley et al.

(10) Patent No.: US 7,550,172 B2
(45) Date of Patent: Jun. 23, 2009

(54) SELECTIVE FEEDING OF STARCH TO INCREASE MILK PRODUCTION IN RUMINANTS

(75) Inventors: David C. Weakley, Eureka, MO (US); Kent J. Lanter, Waterloo, IL (US); Lawrence F. Reutzel, St. Louis, MO (US)

(73) Assignee: Purina Mills, LLC, St. Louis, MO (US)

( * ) Notice: Subject to any disclaimer, the term of this patent is extended or adjusted under 35 U.S.C. 154(b) by 829 days.

(21) Appl. No.: 11/068,410

(22) Filed: Feb. 28, 2005

(65) Prior Publication Data
US 2008/0152754 A1 Jun. 26, 2008

Related U.S. Application Data

(60) Provisional application No. 60/548,848, filed on Feb. 27, 2004.

(51) Int. Cl.
*A23K 1/00* (2006.01)
(52) U.S. Cl. .......................... 426/635; 426/2; 426/658; 426/636; 426/805
(58) Field of Classification Search .................. 426/2, 426/636, 658, 807, 635
See application file for complete search history.

(56) References Cited

U.S. PATENT DOCUMENTS

| | | | |
|---|---|---|---|
| 3,250,622 A | 5/1966 | Brooks .............................. 99/2 |
| 4,508,737 A | 4/1985 | Forest et al. ................... 426/54 |
| 4,615,891 A | 10/1986 | Nocek et al. ................. 426/231 |
| 4,617,276 A | 10/1986 | Nocek .......................... 436/20 |
| 4,957,748 A | 9/1990 | Winowiski ..................... 426/2 |
| 5,023,091 A | 6/1991 | Winowiski ..................... 426/2 |
| 5,143,737 A | 9/1992 | Richardson .................... 426/2 |
| 5,158,791 A | 10/1992 | Nocek et al. ................. 426/231 |
| 6,008,053 A * | 12/1999 | Williams ..................... 436/20 |
| 7,174,672 B2 * | 2/2007 | Beck ...................... 47/58.1 FV |
| 2003/0165487 A1 | 9/2003 | Tricarico et al. ......... 424/94.61 |

FOREIGN PATENT DOCUMENTS

| | | |
|---|---|---|
| EP | 0 043 202 | 4/1984 |
| EP | 1 352 567 | 10/2003 |
| GB | 2 107 567 | 10/1982 |
| WO | WO 91/05482 | 5/1991 |
| WO | WO 93/25616 | 12/1993 |
| WO | WO 96/17525 | 6/1996 |
| WO | WO 01/41795 | 6/2001 |
| WO | WO 02/47473 | 6/2002 |
| WO | WO 02/096191 | 12/2002 |
| WO | WO 03/068256 | 8/2003 |

OTHER PUBLICATIONS

Grant, Richard "Feeding to Maximize Milk Solids", Univ. of Missouri Extension, 5 pages, downloaded from http://extension.missouri.edu/xplor/agguides/dairy/g03110.html., Oct. 1993.*
Mike Allen Formulating Lactating Cow Diets for Carbohydrates, pp. 79-86, Proceedings of the 5th Western Dairy Management Conference, 2001.*
Ishler et al. "Carbohydrate nutrition for lactating dairy cattle", pp. 1-11, Penn State Cooperative Extension publication, 2001.*
Ishler et al. "From Feed to Milk: Understanding Rumen Function" Extension Circular 422, pp. 1-27, 1996.*
Rook, Proc. Nutr. Soc., vol. 38, p. 309, 1979.*
Clark et al., J. Dairy Sci., 63:873-885 1980.*
Fox et al., J. Anim. Sci., 1992, vol. 70:3578-3596), Sniffen et al. (J. Anim. Sci., 1992, vol. 70:3562-3577).*
Sniffen et al., J. Anim. Sci., 1992, vol. 70:3562-3577.*
Van Kempen et al. Near-Infrared Reflectance Spectroscopy in Precision Feed Formulation, J. Appl. Poultry Res. vol. 6, pp. 417-477, 1997.*
Nocek et al., *Site of Digestion of Starch in the Gastrointestinal Tract of Dairy Cows and Its Effect on Milk Yield and Composition*, Journal of Dairy Science, vol. 74, No. 10, 1991, pp. 3598-3612.

* cited by examiner

*Primary Examiner*—C. Sayala
(74) *Attorney, Agent, or Firm*—Westman, Champlin & Kelly, PA; Z. Peter Sawicki

(57) ABSTRACT

The present invention includes a method for improving milk production in a ruminant. An amount of ruminally digestible starch in relation to the dry matter of a feed is manipulated to include a first selected ratio of ruminally digestible starch in relation to the dry matter of the feed which is fed to the ruminant during a first time interval after parturition. After the first time interval, the amount of ruminally digestible starch component in the dry matter of the feed is adjusted to a second ratio, lower than the first ratio, and fed to the ruminant.

39 Claims, 5 Drawing Sheets

SELECTIVE FEEDING OF STARCH TO INCREASE MILK PRODUCTION IN RUMINANTS

CROSS-REFERENCE TO RELATED APPLICATION(S)

The present application is based on and claims the benefit of U.S. provisional patent application Ser. No. 60/548,848, filed Feb. 27, 2004, the content of which is hereby incorporated by reference in its entirety.

BACKGROUND OF THE INVENTION

The present invention relates to methods of feeding ruminants in lactation, and in particular, it relates to methods for optimizing milk production and dry matter intake.

For purposes of this application, the word ruminant will be used to refer to those animals in the suborder of Ruminantia. The most important ruminants are those domesticated animals that fall in the family of Bovidae.

Of particular interest are domesticated cows which are invaluable in supplying milk and meat to the population of most industrialized countries. Milk production in these countries has shifted from small farms to herds that number in the thousands on one farm. Also the business of milk production has become very competitive. In order to stay profitable, farmers have had to optimize the amount of milk produced. Profits are realized more readily when feed is utilized efficiently and when cows produce their maximum amount of milk.

To better understand how to make cows produce more milk, their lactation cycle along with their gastrointestinal system has been studied greatly. There are numerous patents, published patent applications and literature references that describe various feed formulations in an attempt to increase milk production.

Milk secretion in dairy cows is primarily limited by glucose uptake. Nonstructural carbohydrates have been used in attempts to increase milk production. Such nonstructural carbohydrates include starches, soluble sugars and other reserved carbohydrates. Starches are of particular importance since starch in the form of grains such as corn, sorghum, oats, wheat and the like can be purchased at economical prices or grown by the dairy farmer. Starch includes both amylose and amylopectin molecules which are in turn synthesized to glucose for availability to the lactating cow.

However, the dynamics of the ruminant gastrointestinal system are such that when larger quantities of starch are fed, the larger quantities affect the operation of the rumen which in turn affects milk production and dry matter intake (DMI) which in turn affects body maintenance of the cow. Large quantities of starch as a percentage of DMI may result in undesirable pH changes in the rumen which in turn affect microbial activity. Such microbial activity is necessary to digest structural carbohydrates (dry matter) in the rumen. Much has been written about site digestion of starch, how much occurs in the rumen and how much of the undigested starch passes to the abomasum and small intestine and what the affects are on overall milk production. Review of the prior art indicates no specific solution.

Thus the dilemma results of how to increase milk production since to increase more glucose, more starch intake is required which in turn affects rumen performance, and depresses dry matter intake and milk production.

SUMMARY OF THE INVENTION

The present invention includes a method for improving milk production and dry matter intake in a ruminant. An amount of ruminally digestible starch in relation to dry matter of a feed is manipulated to include a first selected ratio of ruminally digestible starch in relation to the dry matter of the feed which is fed to the ruminant during a first time interval after parturition. After the first time interval, the amount of ruminally digestible starch component in the dry matter of the feed is adjusted to a second ratio, lower than the first ratio, and fed to the ruminant.

After approximately 180 days from parturition, the digestible starch component may also be adjusted to an equal or lesser amount in relation to the dry matter of the feed and fed to the ruminant for the remainder of the lactation cycle.

DETAILED DESCRIPTION OF THE PREFERRED EMBODIMENTS

Figure 1:
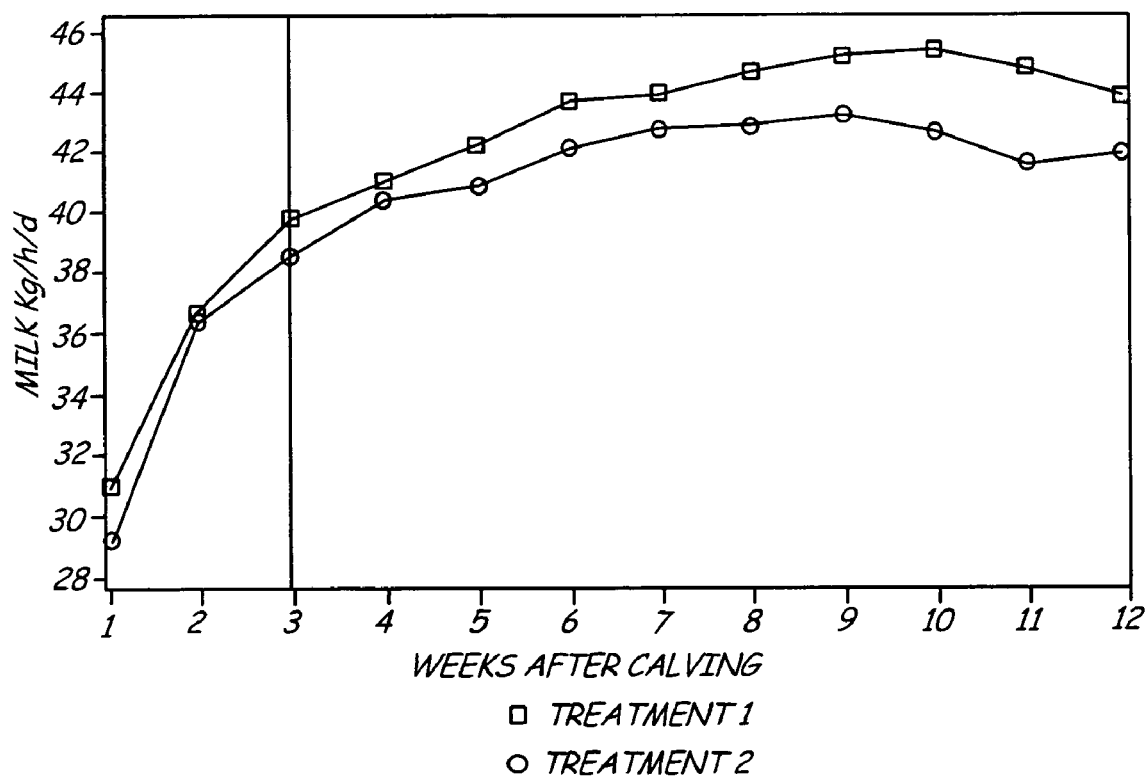
FIG. 1 is a graphical view of milk production comparing treatments 1 and 2.

The present invention includes a method of increasing milk production or dry matter intake or both of a ruminant. The method also includes manipulating milk component synthesis such as protein, fat, fatty acids and lactose. It has been found that by timing the levels of starch intake in relation to dry matter intake (DMI) results in more efficient use of feed in terms of milk production and DMI.

In the first 12 to 30 days (Phase I) in milk (DIM) a higher portion of starch in relation to dry matter in the feed has been found to be beneficial for higher milk production and dry matter intake. After the first approximately 21 to 30 DIM (Phase II), it also has been found that high levels of starch had negative effects on dry matter intake. After approximately six months (180 days) DIM (Phase III), the starch as a percentage of dry matter may be adjusted as needed until the lactation cycle is over.

Levels of starch in Phase I include approximately 14 to 22 weight percent of ruminally digestible starch, and preferably 14 to 20 weight percent and most preferably 16 to 18 weight percent of ruminally digestible starch in relation to the dry matter content of the feed. Phase II includes 12 to 20 weight percent of ruminally digestible starch, preferably 10 to 18 weight percent and most preferably 10 to 16 weight percent of ruminally digestible starch component in relation to the dry matter of the feed with the selected value of ruminally digestible starch component in Phase II being less than in Phase I. The approximate range of ruminally digestible starch component to dry matter in the feed in Phase III is in the approximate range of 7 to 22 weight percent with the actual amount chosen in Phase III being equal, more or less than in Phase II, depending on the energy needs of the animal.

Ruminally digestible starch or starch component refers to those carbohydrate fractions that are digested, degraded, solubilized or otherwise broken down to another form in the rumen. Such starch or starch component includes both starch and sugars. Ruminally digestible starch may also be included within other ruminally digestible carbohydrate fractions, including but not limited to non-fiber carbohydrates, non-structural carbohydrates, soluble carbohydrates, soluble fiber, as well as their inverse measurements: fiber carbohydrates, structural carbohydrates, insoluble carbohydrates, insoluble fiber when such other ruminally digestible carbohydrate fractions are used. Adjustments of these other fractions are less precise and therefore less precise results occur.

Determination of the amount of starch component that is digestible in the rumen is done by any number of methods. The rate and extent of ruminal digestibility of starch component may be determined in vivo through the use of duodenal cannulas. Digestibility of the starch component may also be done in vitro using ruminal fluids. In situ measurements of samples in porous bags deposited within the rumen through surgically placed ports is yet another method. Tabular values or values predicted by computerized animal models of ruminally digestible starch component are available and may also be used. Real time measurements of rumen starch digestibility may also be taken using near infrared reflectance (NIR) spectroscopy. In addition to spectroscopy, spectrophotometric methods that measure absorption, reflectance or transmission of electromagnetic radiation are also within the scope of the present invention.

A nonexhaustive list of sources for the starch component includes: corn grain, corn silage, corn gluten feed, corn germ meal, corn starch, corn byproducts, sorghum grain, sorghum silage, sorghum byproducts, wheat grain, wheat silage, wheat bran, red dog wheat, wheat germ, wheat flour, wheat middlings, wheat byproducts, barley grain, barley silage, barley byproducts, oat grain, oat silage, oat byproducts, bakery byproducts, hominy feed, peas, brewers grains, distillers grains, malt sprouts, rice, rice bran, rice flour, other rice byproducts, cereal feed, sucrose, lactose, glucose, dextrose, or maltose or any combination thereof. In addition other starch sources such as tubers including but not limited to potatoes, yams, sweet potatoes, cassava (tapioca) and arrow root are also suitable.

The starch component may be processed in a number of ways. As used herein in relation to the starch component the terms "processed" or "process" means grinding, steam flaking, steam rolling, extrusion and/or chemically or physically protecting the starch from ruminal digestibility or any other known method of treatment. Chemically or physically protecting the starch component includes but is not limited to aldehyde treatment, heat treatments, resins, binders or coatings. The purpose of processing the starch component is to adjust the rate and extent of ruminal digestibility needed or desired for the particular Phase, either Phase I, II or III.

The rumen digestibility of the starch component may also be manipulated by combining different proportions of the starch sources described previously and/or the types of processing techniques to reach the needed ruminal digestibility value for the particular Phase. The rumen digestibility value needed is determined by the desired outcome, whether it is to maximize milk production, manipulate milk component (protein, fat, fatty acids or lactose content) synthesis and/or maximize DMI. Once the rumen digestibility value of the starch component is chosen, the feed is formulated and fed according to the descriptions of Phase I, II and III as follows:

Phase I: The starch and sugar sources are combined together in a manner to achieve ruminally digestible starch within the approximate range of 14 to 20 weight percent as a percentage of DMI. The selected value in this range being selected to optimize DMI and milk component yield into Phase II, while still maximizing the intake of energy and other essential nutrients needed by the animal in Phase I.

Phase II: The starch and sugar sources are combined together in a manner to achieve a ruminally digestible starch that is less in quantity than in Phase I but within the approximate range of 10 to 18 weight percent as a percentage of DMI. The selected value being selected to optimize DMI and milk component yield while still maximizing the intake of energy and other essential nutrients needed by the animal during Phase II.

Phase III: The starch and sugar sources are combined together in a manner to achieve a quantity of ruminally digestible starch which can be less, equal to or more than the value selected in Phase II but within the approximate range of 7 to 22 weight % as a percentage of DMI. The selected value being chosen to optimize DMI and milk component yield, while still managing the energy intake to meet the requirements of energy and other essential nutrients needed by the animal during Phase III.

To determine the optimum milk production, milk component content and/or DMI for a particular herd of lactating cows and for the type of structural carbohydrate being used in the feed, initial experiments were done to monitor the responses desired. After monitoring responses for example of milk component synthesis and DMI to the initial feeds fed in Phases I, II and III, adjustments are made to the starch component to reach the optimum level of DMI and milk component synthesis as follows:

Increasing the amount of ruminally digestible starch component if milk fat synthesis is high (greater than approximately 3.6 weight percent) and milk protein synthesis is low (less than 3.0 weight percent).

Decreasing the amount of ruminally digestible starch component if milk fat synthesis is low (less than approximately 3.6 weight percent), milk protein synthesis is high (greater than approximately 3.0 weight percent) and DMI is low.

The following examples are provided for illustrative purposes and are not intended to limit the present invention in any manner.

EXAMPLE 1

Objective

To determine the influence of the timing, processing and source of starch feeding on performance of cows in early lactation.

Materials and Methods

Three weeks before anticipated calving, cows were moved to a close-up dry cow facility and fed a diet of (a dry matter (DM) basis): 32.5% corn silage, 32.5% grass hay and 35% Ration BR1 (Table 3) While cows were in the close-up pens, the following information was collected daily:

a. Number of cows in each pen
b. Total mixed ration (TMR) offered
c. TMR weighed back
d. A blood sample was collected 1 week prior to expected calving.

Each week individual composites of corn silage were constructed from individual samples collected each day, Monday through Friday. Each daily subsample was added on top of one another in a large container with a tight lid (the corn silage was kept frozen between sampling). On Friday, the corn silage composite was analyzed for DM determination. Furthermore, individual samples of alfalfa hay, grass hay, close-up ration and each milking ration were collected once per week and composited monthly. At the end of each month, the composite samples (1 each for corn silage, alfalfa hay, grass hay and each ration) were submitted for nutrient analysis.

As the cows calved, the cows were moved into a Tie Stall Unit and assigned, according to the attached schedules (Tables 1 and 2), to rations A or B for the first 3 weeks. Beginning the fourth week post-calving, cows were moved to rations C, D or E, as shown below.

TABLE 1

| Treatment I.D. | 0 to 3 weeks post-calving | 4 to 12 weeks post-calving |
| --- | --- | --- |
| 1 | Diet A | Diet C |
| 2 | Diet B | Diet C |
| 3 | Diet B | Diet D |
| 4 | Diet B | Diet E |

Cows removed from the study were replaced with the next available animal of similar parity (primiparous vs. multiparous).

TABLE 2

| Ingredients | Diet A | Diet B | Diet C | Diet D | Diet E |
| --- | --- | --- | --- | --- | --- |
| | % of Diet DM | | | | |
| Ration A | 48 | | | | |
| Ration B | | 48 | | | |
| Ration C | | | 55 | | |
| Ration D | | | | 55 | |
| Ration E | | | | | 55 |
| Corn Silage N48-V8 | 26 | 26 | 22.5 | 22.5 | 22.5 |
| Alfalfa Hay | 26 | 26 | 22.5 | 22.5 | 22.5 |

TABLE 3

| Component | Ration A | Ration B | Ration C | Ration D | Ration E | Ration BRI |
| --- | --- | --- | --- | --- | --- | --- |
| Main Formula | | | | | | |
| 38% Beef Tallow Nugget | 7.9808 | 7.9808 | 10.2778 | 4.4973 | 7.2742 | |
| Sub-Total | 7.9808 | 7.9808 | 10.2778 | 4.4973 | 7.2742 | |
| Premix Checker | | | | | | |
| Super Fine Ground Corn | | 25.4983 | | | | |
| Protected Soybean Meal | 5.0997 | 5.0997 | | | | |
| Ground Corn Fine | 51.6133 | 26.1150 | 33.4016 | 55.5244 | 26.3836 | 24.6867 |
| Ground Milo | | | | | 26.5121 | |
| Ground Soybean Hulls | | | 28.0829 | 9.7364 | 10.3949 | 42.1695 |
| Dehulled Soymeal | 28.9721 | 28.9721 | 22.5352 | 24.4129 | 23.4422 | 25.1685 |
| Calcium Carbonate | 1.6343 | 1.6343 | 1.1873 | 1.4895 | 1.5127 | 1.8251 |
| Dicalcium Phosphate | 0.9826 | 0.9826 | 1.2443 | 1.0474 | 1.1952 | 0.7916 |
| Salt | 0.9643 | 0.9643 | 0.8433 | 0.8358 | 0.8406 | 0.6632 |
| Urea | 1.0199 | 1.0199 | 0.8920 | 0.8840 | 0.8891 | 1.2159 |
| Liquid Fat | 0.9367 | 0.9367 | 0.8192 | 0.8119 | 0.8165 | |
| Molasses | | | | | | 2.0015 |
| Magnesium Oxide 51 | 0.2497 | 0.2497 | 0.2173 | 0.2346 | 0.2321 | 0.9327 |
| Mag-Pot-Sulfate | 0.1639 | 0.1639 | 0.2015 | 0.2282 | 0.2090 | 0.0086 |
| Sub-Total | 91.6365 | 91.6365 | 89.4247 | 95.2051 | 92.4281 | 99.4633 |
| Micro 1 | | | | | | |
| Ground Corn Fine | 0.1700 | 0.1700 | 0.1270 | 0.1287 | 0.1278 | 0.2045 |
| VIT A | 0.0281 | 0.0281 | 0.0177 | 0.0175 | 0.0176 | 0.0321 |
| VIT E | 0.0247 | 0.0247 | 0.0156 | 0.0154 | 0.0155 | 0.0771 |
| VIT D | 0.0107 | 0.0107 | 0.0068 | 0.0067 | 0.0067 | 0.0110 |
| Selenium | 0.0918 | 0.0918 | 0.0803 | 0.0796 | 0.0800 | 0.1094 |
| Trace Min D | 0.0574 | 0.0574 | 0.0502 | 0.0497 | 0.0500 | 0.1026 |
| Sub-Total | 0.3827 | 0.3827 | 0.2975 | 0.2976 | 0.2977 | 0.5367 |
| Total | 100.00 | 100.00 | 100.00 | 100.00 | 100.00 | 100.00 |

All diets were fed as TMR's, ad libitum, to achieve a 5-10% daily weighback.

Dry matter content of corn silage was determined weekly and "as fed" proportions changed if moisture varied by more than 2%.

TABLE 4

Sampling Schedule (Dry Cows - Prior to Parturition):

| Parameter | Sampling Schedule |
| --- | --- |
| TMR Offered, weight | Daily (no sample) |
| TMR Weighed Back, weight | Daily (no sample) |
| Number of cows in each pen | Daily |
| Body Condition score | Weekly, 2 independent scores |
| Health data | Daily |
| Ration DC475BR1 | Sampled weekly, composite monthly |
| Grass Hay | Sampled weekly, composite monthly |
| Blood samples | 1 week pre-calving |

TABLE 5

Sampling Schedule (Lactating Cows):

| Parameter | Sampling Schedule |
|---|---|
| Milk Production | Daily - am/pm |
| Milk Composition | p.m. Monday-Friday |
| TMR Offered, weight | Daily (no sample) |
| TMR Weighed Back, weight | Daily (no sample) |
| Body Weight | Twice daily |
| Body Condition Score | Weekly, 2 independent scores |
| Corn Silage | Sampled daily, composite monthly |
| Alfalfa Hay | Sampled weekly, composite monthly |
| Milking Rations | Sampled weekly, composite monthly |
| Blood samples | Day 0, 2 and wk 1, 2, 4, 6, 8 and 12 |
| Reproductive data/health | Daily records |

Health and reproductive status: A daily record of all calving and reproductive events, as well as disorders and removals from the study were maintained.

Blood Sampling: Two separate samples of blood were collected from the tail vein into red and black-top tubes (beta-hydroxybutyric acid (BHBA), triglyceride and normal blood chemistry panel analyses; serum) and gray-top tubes (non-esterified fatty acids (NEFA), glucose and lactate analyses; plasma), respectively. The gray-top sample was placed in an ice-water bath immediately after collection. The red-top tube was held at room temperature. Blood sampling during the dry period was conducted weekly with any cows eligible for sampling during that week sampled on a single day so that sampling, sample processing and analyses could be consolidated.

Blood sampling post-calving was as follows: If a cow gave birth on the weekend, a gray-top tube was not be collected for the 0 day sample. Regarding the day 2 blood sample: Where cows calf between the days of Saturday and Wednesday, the samples were taken on day 2 post-calving. Cows calving on Thursday were sampled on Friday afternoon and cows calving on Friday were sampled on Monday morning. Beginning with the week 1 blood sample, the sampling of the cows giving birth the previous Saturday were sampled on Friday, while the cows giving birth the previous Sunday were sampled on Monday.

Discussion

Results of observations of early lactation, mid-lactation and metabolism studies (4750 observations) indicated that the negative effects of high levels of starch on dry matter intake seemed to appear after 30 DIM, peaked around 100 DIM and subsided around 180 DIM (although there were fewer data past 180 DIM). This suggests that there are advantages to obtaining a lesser proportion of ME intake from starch as cows approach 100 DIM. Alternatively, using sources of starch that have a slower rate, but similar extent, of digestion, compared with corn, may obviate the DMI depression.

This example was designed to look at the timing of starch feeding (before verses after 21 DIM). During the first 3 weeks after calving, cows were fed higher corn diets, where the corn was either in flour or fine ground form, to test the hypothesis that a more rapid propionate fermentation may cause a down regulation of tissue mobilization, reducing blood NEFA levels and the incidence of ketosis. After 3 weeks, cows were changed over to either low (20%) or high (28%) starch diets. The high starch diet had either all the supplemental starch in the form of fine ground corn or a 50% replacement with milo (which has a lower rate of starch fermentation).

Phase I (0-3 Weeks Post Calving)

There were no significant effects by treatment on milk production, fat corrected milk production, protein percent or yield, fat percent or yield or average daily gain (ADG) (See Table 6)

DMI tended to be depressed (P<0.09) by the corn flour treatment (Table 6)

However, despite this lack of effect by treatment during the period imposed (0-3 weeks post-calving), there was a tendency for a carryover effect into Phase II (4-12 weeks post-calving. See Table 7) on improving milk production by approximately 2 kg/day (P<0.18, Table 7).

TABLE 6

Milk production, milk components and dry matter intake results (Weeks 1-3)

| Week 1-3 | Fine Ground Corn | Fine Ground Flour | Standard Error |
|---|---|---|---|
| Number Cows Finished | 23 | 66 | |
| Milk Kg/head/day | 34.8 | 35.3 | 0.907 |
| Fat Corrected Milk Kg/head/day | 34.2 | 34.3 | 0.942 |
| Milk Fat % | 3.93 | 3.84 | 0.0818 |
| Fat Kg/head/day | 1.35 | 1.34 | 0.0437 |
| Protein % | 3.41 | 3.39 | 0.0560 |
| Protein Kg/head/day | 1.16 | 1.18 | 0.0267 |
| Dry Matter Intake Kg | 15.28 | 14.44 | 0.351 |
| Body Score | 3.06 | 2.94 | 0.0646 |

TABLE 7

Milk production, milk components and dry matter intake results (Weeks 4-12)

| Week 4-12 | Fine Ground Corn | Fine Ground Flour | Standard Error |
|---|---|---|---|
| Number Cows Finished | 23 | 22 | |
| Milk Kg/head/day | 42.1 | 44.0 | 0.999 |
| Fat Corrected Milk Kg/head/day | 35.0 | 36.3 | 0.871 |
| Milk Fat % | 2.89 | 2.87 | 0.0782 |
| Fat Kg/head/day | 1.21 | 1.25 | 0.0410 |
| Protein % | 2.83 | 2.83 | 0.0330 |
| Protein Kg/head/day | 1.19 | 1.24 | 0.0278 |
| Average Daily Gain Kg | 0.078 | 0.191 | 0.0917 |
| Dry Matter Intake Kg | 20.7 | 21.0 | 0.434 |
| Body Score | 2.69 | 2.55 | 0.0515 |

Phase II (4-12 Weeks Post Calving)

All cows were on a common diet for the first 3 weeks. Consequently, there were not (and should not have been) any significant differences in production. When half the corn in treatment 3 was replaced with milo in Treatment 4, fat corrected milk (FCM) production was significantly improved by 2.6 kg/day (P<0.01). (Table 8) When half the corn in treatment 3 was replaced with milo in treatment 4, milk fat percentage was improved by 0.34 percentage units, and milk fat yield was improved by 0.18 kg/day (P<0.01), while milk protein percentage and yield remained relatively unchanged. When half the corn in treatment 3 was replaced with milo in treatment 4, dry matter intake (DMI) was improved by 1.0 kg/day (P<0.01). There were no significant differences in DMI, milk production or milk components, between treatments 2 and 4, suggesting that a high starch diet can perform as well as an isocaloric diet, containing more of its energy from fat and less from starch, provided that the degradability of the starch is reduced by the substitution of half the corn with milo. Body condition score was improved with the higher starch treatments (treatments 3 and 4), vs. the isocaloric diet (treatment 2), containing more of its energy from fat and less from starch.

TABLE 8

Phase II (4-12 weeks post-calving)
Influence of the timing, processing and source of starch feeding on performance of cows in early lactation.

|  | 20% Starch Fine Ground Corn | 28% Starch Fine Ground Corn | 28% Starch Fine Ground Corn and Milo | Standard Error | (1) | (2) | (3) | (4) |
|---|---|---|---|---|---|---|---|---|
| Treatment | 2 | 3 | 4 |  |  |  |  |  |
| Milk Kg/head/day | 44.2 | 44.4 | 43.9 | 0.837 | — | — | — | — |
| Fat Corrected Milk Kg/head/day | 36.9b | 34.9a | 37.5b | 0.673 | .03 | .17 | .03 | .01 |
| Milk Fat % | 2.96b | 2.64a | 2.98b | 0.0828 | .01 | — | .01 | .01 |
| Fat Kg/head/day | 1.28b | 1.14a | 1.32b | 0.0361 | .01 | — | .01 | .01 |
| Protein % | 2.84 | 2.83 | 2.82 | 0.0334 | — | — | — | — |
| Protein Kg/head/day | 1.26 | 1.24 | 1.25 | 0.0262 | — | — | — | — |
| Average Daily Gain Kg | 0.275 | 0.258 | 0.071 | 0.119 | — | .16 | — | — |
| Dry Matter Intake Kg | 21.4 | 20.4 | 21.4 | 0.414 | .13 | — | .06 | .12 |
| Body Score | 2.39a | 2.67b | 2.57b | 0.0599 | .01 | — | .01 | — |

PR > F if < .20 for:
(1) Treatment
(2) Treatment by Parity
(3) Treatment 2 vs 3
(4) Treatment 3 vs 4
Means in the same row not followed by a common letter differ (P < .05) using LSD procedure.

CONCLUSIONS

Phase I (0-3 Weeks Post Calving):
While substituting half of the ground corn with corn flour in the diet of cows fed for the first 3 weeks post-calving, did not significantly affect production in the first 3 weeks, there was a tendency for carry-over improvements in milk yield over the next 9 weeks (4-12 weeks post-calving. See FIG. 1). A likely reason for this response not being statistically significant, may have been due to a tendency (P<0.09) for a lower DMI with the corn flour treatment (diet B), during the first 3 weeks post-calving. The depressed DMI may have been due to exceeding the optimum of ruminally degraded starch in the diet for the first 3 weeks post-calving.

Figure 2:
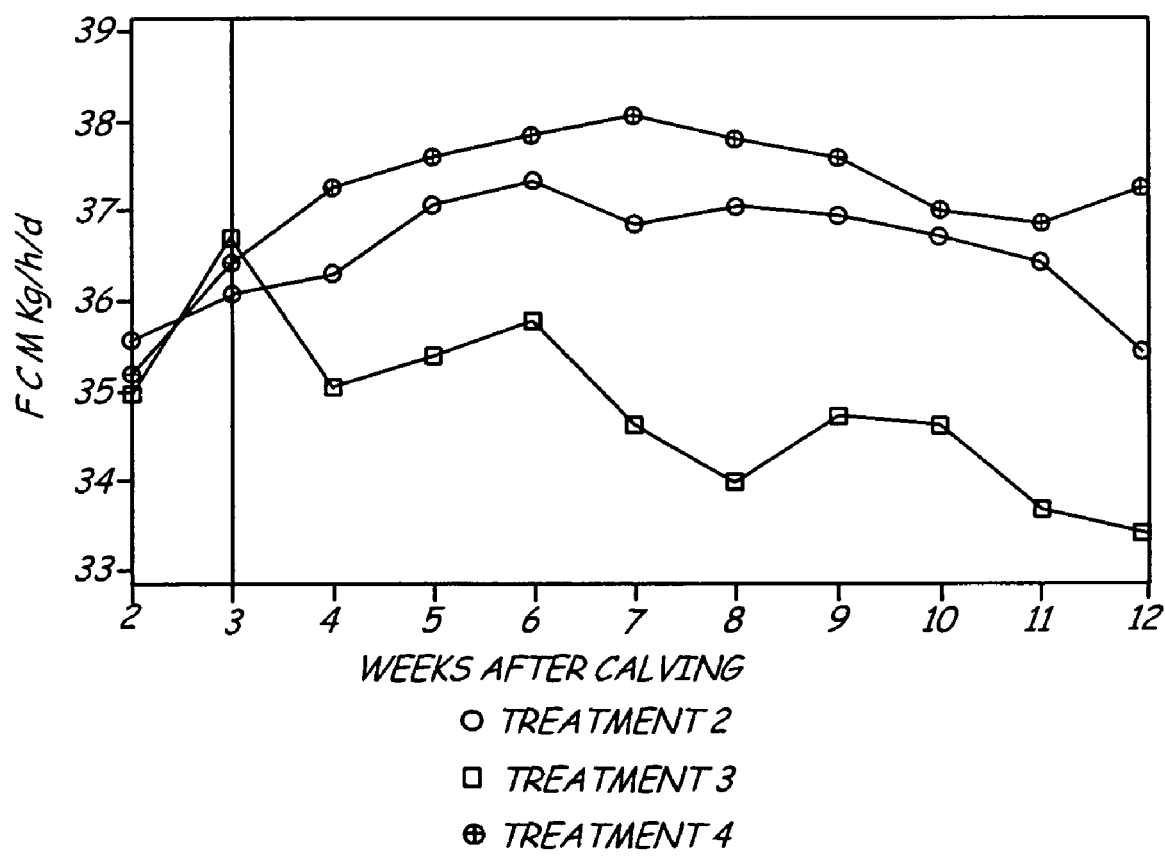
FIG. 2 is a graphical view of fat corrected milk comparing treatments 2, 3 and 4.
Figure 3:
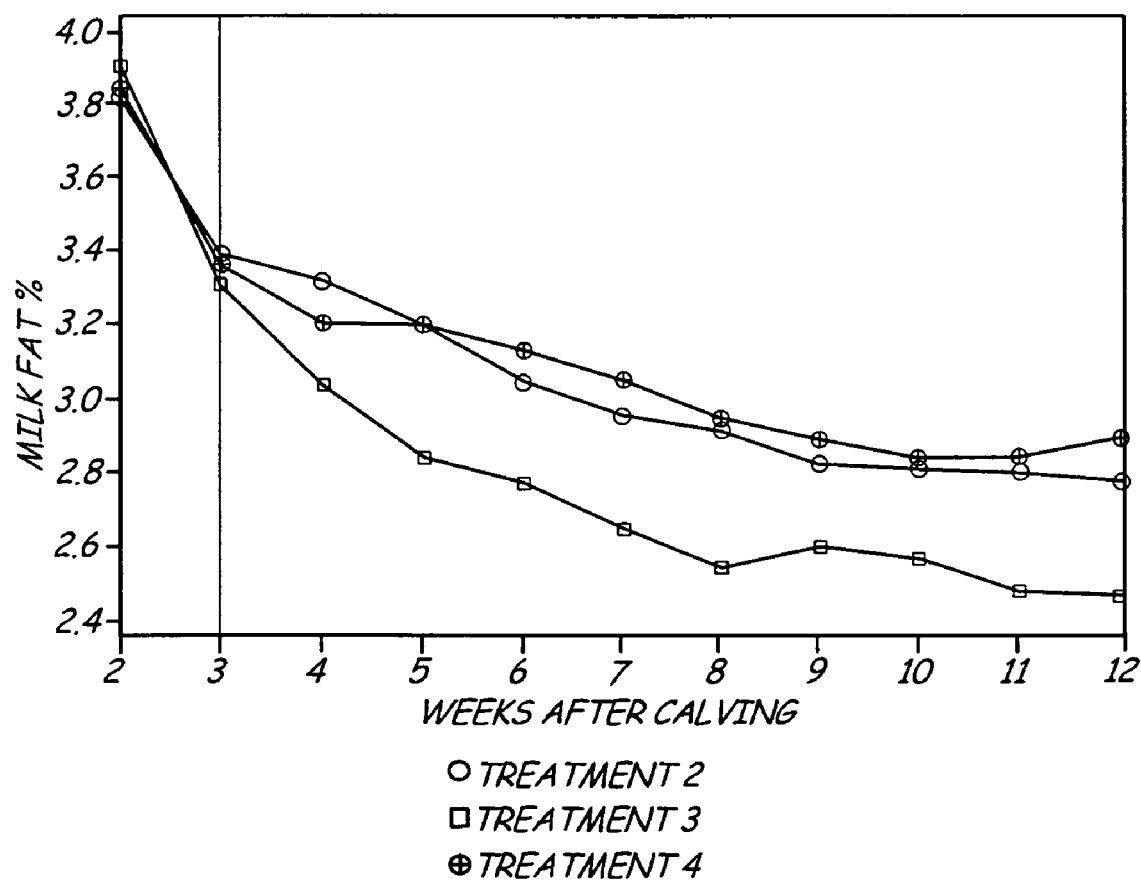
FIG. 3 is a graphical view of milk fat production comparing treatments 2, 3 and 4.
Figure 4:
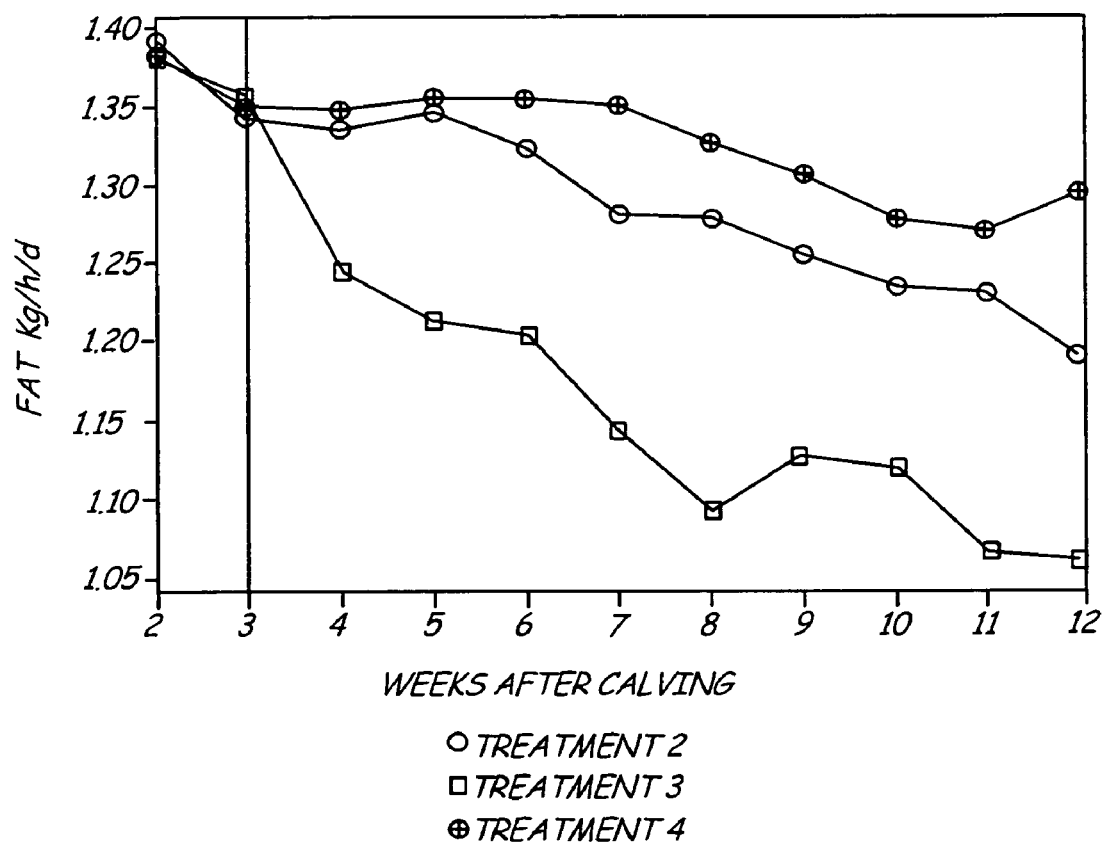
FIG. 4 is a graphical view of fat yield comparing treatments 2, 3 and 4.
Figure 5:
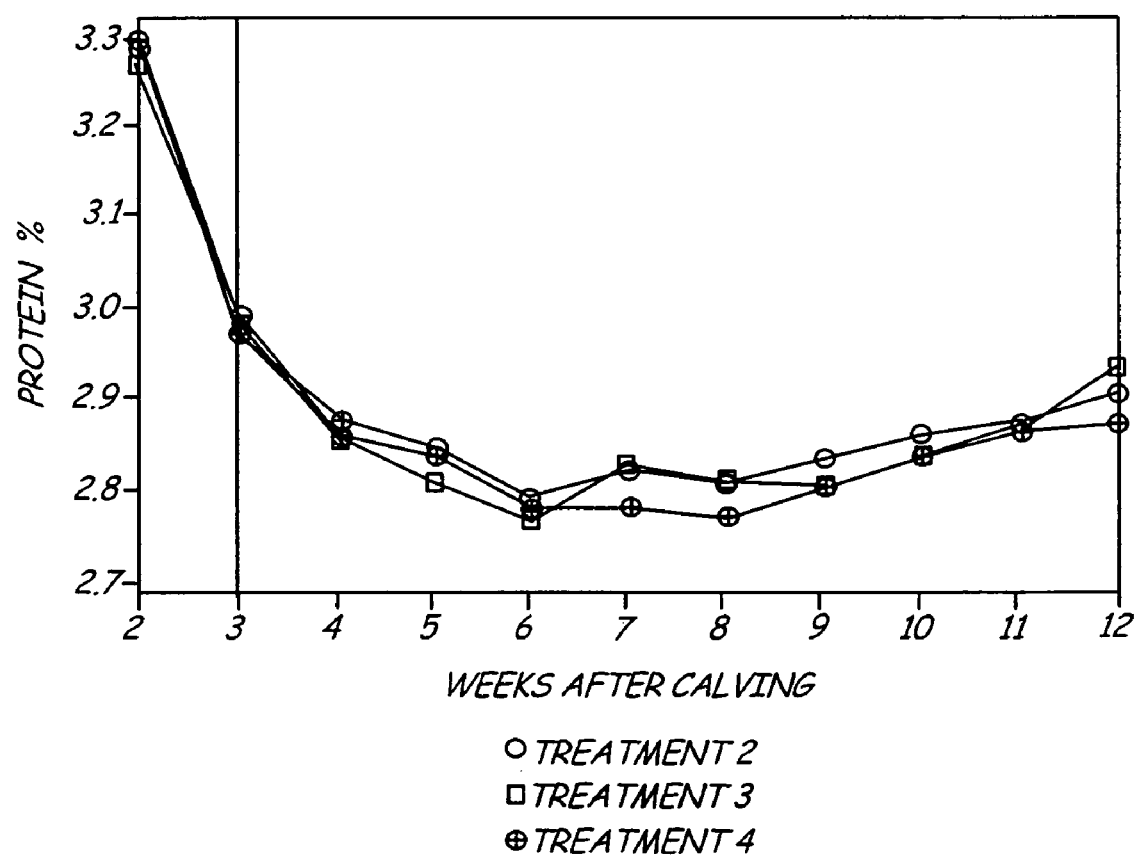
FIG. 5 is a graphical view of percent protein in milk production comparing treatments 2, 3 and 4.

Phase II (4-12 Weeks Post Calving):
The depression in FCM and milk fat percentage and yield (See FIGS. 2, 3 and 4), created by feeding excessive amounts of ruminally degraded starch (treatment 3), was corrected by replacing half of the corn with the more slowly ruminally degraded starch source, milo. The level of FCM and milk fat production observed with the milo treatment (treatment 4), was similar to that observed with the lower starch, higher fat treatment (treatment 2), suggesting that a high starch diet can perform as well as an isocaloric diet, containing more of its energy from fat and less from starch, provided that the degradability of the starch is reduced by the substitution of half the corn with milo. The improvement in FCM and milk fat production, with the milo treatment, was accomplished without compromising milk protein production (See FIG. 5).

EXAMPLE 2

To better determine the dietary levels of starch needed for Phase II (weeks 4-12) 12 Holstein cows were subjected to three treatments in one period of feeding. The animals were allowed to adjust to diets for a minimum of two weeks once full treatment feed intake was achieved. During the adjustment phase, feed offerings and refusal were measured daily, but no samples collected. After completion of the adjustment period, feed, milk, urine and feces samples were collected for five days. All animals were fed the assigned diets according to the proportions shown in Table 9. Table 10 shows the composition of the treatments used.

TABLE 9

|  | Treatments | | |
|---|---|---|---|
|  | 1 | 2 | 3 |
|  | % of Dry Matter | | |
| Ration A | 30 |  |  |
| Ration B |  | 43.3 |  |
| Ration C |  |  | 56.7 |
| Alfalfa Hay | 52.5 | 42.5 | 32.5 |
| Silage | 17.5 | 14.2 | 10.8 |

TABLE 10

| Ration | % Forage | % Starch |
|---|---|---|
| A | 70 | 7 |
| B | 57 | 17 |
| C | 43 | 27 |

Alfalfa hay was from a consistently homogenous supply and the diets were offered three times daily. Forage silage and alfalfa hay were fed as a mix.

Animals had diets available to them at all times (offered three times daily) but dry matter intake among all animals was not allowed to vary by more than 0.5% of body weight during the collection week. Dry matter intakes were fixed three days prior to and during the five day collection period. During the five days, composite was made of daily subsamples of each dietary ingredient (rations and forage mix) collected during each proceeding day of the collection period.

Samples of feces, milk and urine were collected at a constant percentage daily from each animal during the five days. A five day composite was constructed for each animal.

A summary of the results of this Example are included in Table 11 set forth below.

TABLE 11

Influence of Three Ratios of Dietary Fiber:Starch in Lactating Cows in Mid-Lactation (Phase II).
Least Squares Treatment Means

| $ADF_1$:Starch | 33:7% | 28:17% | 22:27% | Standard Error | (1) | (2) | (3) |
|---|---|---|---|---|---|---|---|
| Milk, kg/day | 22.8 | 27.8 | 30.7 | 2.77 | — | .11 | — |
| F.C.M. kg/day | 20.2 | 25.0 | 24.2 | 1.61 | .15 | .15 | .20 |
| Fat, kg/day | 0.737a | 0.926b | 0.793ab | 0.0420 | .04 | — | .02 |
| Protein, kg/day | 0.655 | 0.831 | 0.857 | 0.0585 | .10 | .07 | — |
| Dry Matter Intake, kg/day | 22.4 | 19.8 | 22.3 | 1.06 | — | — | .10 |
| Nitrogen Intake, kg/day | 0.674 | 0.596 | 0.645 | 0.0317 | — | — | .15 |
| Milk Nitrogen % of Intake | 17.6a | 25.2b | 23.3ab | 1.72 | .05 | .07 | .07 |
| Gross Energy Intake Megacalories | 98.3 | 86.9 | 98.2 | 4.58 | — | — | .09 |
| Digested Energy, Megacalories/Kg Dry Matter | 2.82a | 2.89ab | 3.04b | 0.0487 | .07 | .03 | — |
| Retained Energy, % of Gross Energy | 45.3 | 40.6 | 47.6 | 2.01 | .13 | — | .06 |
| Milk Energy, % of Gross Energy | 15.1a | 21.7b | 18.1ab | 1.17 | .02 | .14 | .01 |

$_1$ADF - Acid Detergent Fiber
PR > F if < .20 for:
(1) Treatment
(2) Linear
(3) Deviation from Linear
Means in the same row not followed by a common letter differ (P < .05) using LSD procedure.

As can be seen from Table 11 above, milk fat production was greatest for the intermediate (17%) starch containing diet. A linear effect of increasing dietary starch levels resulted in increasing milk protein production, but the difference between the 17% and the 27% starch containing diets was small.

The conversion of dietary nitrogen into milk nitrogen (milk nitrogen, % of intake) was greatest with the intermediate (17%) starch containing diet.

While increasing levels of dietary starch resulted in the linear increase in the digestible energy content of the diet, milk energy as a percent of gross energy was greatest (P=0.01), and retained energy as a percent of gross energy was lowest (P=0.06) with the 17% starch containing diet.

CONCLUSIONS

Even though increasing levels of dietary starch in the diet caused an increase in the energy density of the diet, there was an optimal level of dietary starch (17%) that promoted the greatest amount of energy deposition into milk energy. The two sub-optimum dietary starch levels (7% and 27%), on either side of the optimum level, diverted more energy into retained energy (body stores) and away from milk energy. At an assumed ruminal degradability of 60% of starch intake, this optimum level would equate to a level of approximately 10% of ruminal degradable starch, as a percent of dry matter intake.

EXAMPLE 3

This Example evaluates four levels of dietary starch (10, 18, 26 and 34%), utilizing consistent dietary and experimental conditions, in an attempt to test for non-linear effects on rumen function and digestibility. No attempt was made to add fat to maintain all diets isocaloric, to avoid the interaction from potential ruminal fat effects.

Four ruminally fistulated steers and four intestinally fistulated steers were housed and fed in a tie stall area.

Four treatments were applied to each group of four steers in a 4×4 Latin Square design set forth below.

| | Ruminally Fistulated Steer # | | | | Intestinally Fistulated Steer # | | | |
|---|---|---|---|---|---|---|---|---|
| Period | 1 | 2 | 3 | 4 | 1 | 2 | 3 | 4 |
| | Treatment Assignment | | | | | | | |
| I | 3 | 4 | 1 | 2 | 3 | 4 | 1 | 2 |
| II | 2 | 3 | 4 | 1 | 2 | 3 | 4 | 1 |
| III | 4 | 1 | 2 | 3 | 4 | 1 | 2 | 3 |
| IV | 1 | 2 | 3 | 4 | 1 | 2 | 3 | 4 |

Diets were fed as total mixed rations described in Tables 12 and 13.

TABLE 12

| | Treatments | | | |
|---|---|---|---|---|
| | 1 | 2 | 3 | 4 |
| | % of Diet Dry Matter | | | |
| Ration A | 55 | | | |
| Ration B | | 55 | | |
| Ration C | | | 55 | |
| Ration D | 22.5 | | | 55 |
| Alfalfa Hay | 22.5 | 22.5 | 22.5 | 22.5 |
| Dual Purpose Silage | 22.5 | 22.5 | 22.5 | 22.5 |

TABLE 13

| Treatment | % Starch | Starch Source |
|---|---|---|
| 1 | 10 | Fine Ground Corn |
| 2 | 18 | Fine Ground Corn |
| 3 | 26 | Fine Ground Corn |
| 4 | 34 | Fine Ground Corn |

Once animals were on full treatment feed, dry matter intakes did not vary by more than 0.4% of body weight. Each period, the animals were allowed to adjust to the diets for a minimum of two weeks once full treatment feed intake was achieved.

Composites were made of daily subsamples of the dietary ingredients equal duodenal, ileal and rumen fluid samples and bacteria samples were collected and analyzed. The results of the analysis are listed in Table 14 set forth below.

TABLE 14

Nutrient digestibility ("Dry Matter basis", unless noted differently)

| % Starch | 10 | 18 | 26 | 34 | Standard Error | (1) | (2) | (3) | (4) |
|---|---|---|---|---|---|---|---|---|---|
| Dry Matter Intake kg/day | 7.89 | 7.55 | 7.80 | 7.62 | 0.197 | — | — | — | — |
| Nitrogen Intake, kg/day | 0.233 | 0.222 | 0.227 | 0.221 | 0.00544 | — | — | — | — |
| Nitrogen Microbial Duodenal, kg/day | 0.0906 | 0.0802 | 0.0817 | 0.0819 | 0.00495 | — | — | — | — |
| Microbial Efficiency grams nitrogen/kg feed organic matter digested | 23.8 | 19.5 | 20.0 | 22.2 | 1.94 | — | — | .15 | — |
| Nitrogen Digested, % of Intake | 70.3a | 73.0b | 70.7ab | 68.8a | 0.620 | .03 | .05 | .02 | .13 |
| Gross Energy Intake MCAL | 34.6 | 33.7 | 34.8 | 34.3 | 0.860 | — | — | — | — |
| Digestible Energy, Megacalories/kg Dry Matter | 3.10a | 3.34b | 3.26ab | 3.16ab | 0.0617 | .15 | — | .04 | — |
| Neutral Detergent Fiber Intake, kg/day | 3.71c | 3.09b | 2.76b | 2.09a | 0.0955 | .01 | .01 | — | — |
| Neutral Detergent Fiber Rumen Digested, % of Intake | 46.7 | 54.3 | 44.7 | 35.2 | 5.94 | — | .14 | — | — |
| Neutral Detergent Fiber digested in Rumen, % Dry Matter Intake | 22.0b | 22.7b | 15.0ab | 9.7a | 2.16 | .03 | .01 | — | — |
| Neutral Detergent Fiber Digested, % of Intake | 62.8b | 64.2b | 56.3ab | 44.3a | 3.98 | .05 | .01 | .15 | — |
| Starch Wenger (Enzymatic) Starch Intake, kg/day | 0.96a | 1.43b | 2.04c | 2.75d | 0.0677 | .01 | .01 | .14 | — |
| Starch digested in Rumen, % Dry Matter Intake | 3.77a | 11.39ab | 16.02bc | 22.37c | 2.13 | .01 | .01 | — | — |
| Starch Digested % of Intake | 95.7a | 96.9ab | 97.7b | 97.3ab | 0.552 | .13 | .05 | — | — |

PR > F if < .20 for:
(1) Treatment
(2) Linear
(3) Quadratic
(4) Cubic
Means in the same row not followed by a common letter differ (P < .05) using LSD procedure.

Neither dry matter intake, protein nitrogen (N) intake, microbial protein flow to the small intestine or efficiency of microbial protein synthesis were affected by any of the treatments.

While gross energy intake was similar across treatments, there was a quadratic effect (P=0.04) by treatment on digestible energy, with the two intermediate starch levels supporting the greatest digestible energy density (mcal/kg) (Table 14).

Starch intake increased with increased starch level in the diet, resulting in increasing levels of ruminally degradable starch ranging from a low of 3.8% to a high of 22.4% of dry matter intake. While total starch digestibility was increased linearly (P=0.05) by increasing dietary starch, the differences were biologically unimportant (Table 14).

Neutral detergent fiber intake decreased with increasing starch levels, as expected. Ruminal neutral detergent fiber digestion (% of neutral detergent fiber intake) was numerically greatest with the 18% starch treatment. Ruminal neutral detergent fiber digestion (% of dry matter intake) and total tract neutral detergent fiber digestion (% of neutral detergent fiber intake) were greatest (P=0.01) for the two lowest starch treatments (Table 3).

CONCLUSIONS

The data in Table 14 show that optimal levels exist for ruminal starch degradability that maximize ruminal neutral detergent fiber digestibility. Ruminal neutral detergent fiber digestibility was maximized at levels of ruminal degradable starch below 16.02% of dry matter intake with the highest numerical ruminal neutral detergent fiber digestibility, protein nitrogen digestibility and digestible energy concentration occurring at 11.39% of dry matter intake as ruminal degradable starch. At these lower levels of ruminal starch degradability, microbial protein synthesis was not adversely affected. Therefore, at levels of ruminal degradable starch below 16.02% conditions were optimal for neutral detergent fiber digestibility, which should in turn create conditions that are optimal for synthesizing milk fat in lactating dairy cattle.

Although the present invention has been described with reference to preferred embodiments, workers skilled in the art will recognize that changes may be made in form and detail without departing from the spirit and scope of the invention.

What is claimed is:

1. A method for improving milk production and/or dry matter intake in a cow after parturition, the method comprising:
    manipulating an amount of a ruminally digestible starch component in the dry matter of a feed wherein the amount of ruminally digestible starch component in the dry matter of the feed is adjusted to a first selected amount during a first time interval and during a second time following the first time interval, the amount of the ruminally digestible starch component in the dry matter in the feed is adjusted to a second amount, lower than the first amount, and fed to the cow.

2. The method of claim 1 wherein the first time interval ends approximately 21 to 30 days after parturition.

3. The method of claim 1 wherein the first selected amount is in an approximate range of 14 to 22 weight percent of the ruminally digestible starch component in relation to the dry matter of the feed.

4. The method of claim 1 wherein the second time interval starts approximately 21 to 30 days after parturition.

5. The method of claim 1 wherein the second selected amount is in the approximate range of 12 to 20 weight percent of ruminally digestible starch component in the dry matter of the feed.

6. The method of claim 1 further including adjusting the amount of digestible starch after approximately 180 days from parturition in an approximate range of 7 to 22 weight percent of the ruminally digestible starch component in the dry matter of the feed.

7. The method of claim 1 further including:
    analyzing milk from the cow for milk fat content and;
    increasing the amount of the ruminally digestible starch component if the milk fat content is high.

8. The method of claim 1 further including:
    analyzing milk from the ruminant for milk fat content; and
    decreasing the amount of ruminally digestible starch if the milk fat content is low.

9. The method of claim 1 further including measuring rumen digestibility of the ruminally digestible starch component in vitro.

10. The method of claim 1 further including selecting the ruminally digestible starch component based on predetermined digestibility values.

11. The method of claim 1 further including measuring the rumen digestibility of the ruminally digestible starch component via duodenal cannulas in the ruminant.

12. The method of claim 1 further including measuring the rumen digestibility of the ruminally digestible starch component by in situ measurements of the ruminally digestible starch component in pourous bags in the rumen.

13. The method of claim 1 further including measuring the rumen digestibility of the ruminally digestible starch component by spectrophotometric methods.

14. The method of claim 1 further including measuring the rumen digestibility of the ruminally digestible starch component by infrared reflectance spectroscopy.

15. The method of claim 1 wherein the ruminally digestible starch component of either the first feed, second feed or third feed includes:
    corn grain, corn silage, corn gluten feed, corn germ meal, corn starch, corn byproducts, sorghum grain, sorghum silage sorghum byproducts, wheat grain, wheat silage, wheat bran, red dog wheat, wheat germ, wheat flour, wheat middlings, wheat byproducts, barley grain, barley silage, barley byproducts, oat grain, oat silage, oat byproducts, bakery byproducts, hominy feed, peas, brewers grains, distillers grains, malt sprouts, rice, rice bran, rice flour, rice byproducts, cereal feed, sucrose, lactose, glucose, dextrose, maltose, cassava, potatoes or other starchy tubers or any combination thereof.

16. The method of claim 1 wherein the first or second selected amount of the ruminally digestible starch component is obtained by combining starch ingredients having different rumen digestibilities.

17. The method of claim 13 wherein the ruminally digestible starch component is processed to achieve the first selected amount or the second selected amount.

18. The method of claim 1 wherein the ruminally digestible starch component ratio of the first selected amount or the second selected amount is achieved by including non-fiber carbohydrates, non-structural carbohydrates, soluble carbohydrates, or soluble fiber, or any combination thereof.

19. The method of claim 1 wherein ruminally digestible starch component, the second feed includes milo.

20. A method for improving milk production and/or dry matter intake in a ruminant, the method comprising:
    feeding the ruminant during a first time interval after parturition a first feed having a ruminally digestible starch component being in an approximate range of 14 to 22 weight percent of dry matter of the first feed;
    feeding the ruminant during a second time interval after the first time interval, a second feed having a ruminally digestible starch component being in an approximate range of 12 to 20 weight percent of the dry matter of the second feed; and
    wherein the ruminally digestible starch component of the first feed is a greater portion of the dry matter than the ruminally digestible starch component of the second feed.

21. The method of claim 20 wherein the first time interval ends approximately up to 21 to 30 days after parturition.

22. The method of claim 21 wherein the second time interval starts approximately 21 to 30 days after parturition.

23. The method of claim 20 further including:
    feeding the ruminant approximately 180 days from parturition a third feed having a ruminally digestible starch component in an approximate range of 7 to 22 weight percent of dry matter of the third feed.

24. The method of claim 20 further including:
    analyzing milk from the ruminant for milk fat content;
    increasing the amount of ruminally digestible starch component in the first feed, or the second feed if the milk fat content is high.

25. The method of claim 20 further including:
    analyzing milk from by the ruminant for milk fat; and
    decreasing the amount of ruminally digestible starch component in either the first feed or second feed if the milk fat content is low.

26. The method of claim 20 further including measuring the rumen digestibility of the ruminally digestible starch component in vitro.

27. The method of claim 20 further including selecting the ruminally digestible starch component based on predetermined digestibility values.

28. The method of claim 20 further including measuring the rumen digestibility of the ruminally digestible starch component via duodenal cannulas in the ruminant.

29. The method of claim 20 further including measuring the rumen digestibility of the ruminally digestible starch component by in situ measurements of the ruminally digestible starch component in pourous bags in the rumen.

30. The method of claim 20 further including measuring the rumen digestibility of the ruminally digestible starch component by spectrophotometric methods.

31. The method of claim 20 further including measuring the rumen digestibility of the ruminally digestible starch component by infrared reflectance spectroscopy.

32. The method of claim 20 wherein the ruminally digestible starch component comprises:

corn grain, corn silage, corn gluten feed, corn germ meal, corn starch, corn byproducts, sorghum grain, sorghum silage, sorghum byproducts, wheat grain, wheat silage, wheat bran, red dog wheat, wheat germ, wheat flour, wheat middlings, wheat byproducts, barley grain, barley silage, barley byproducts, oat grain, oat silage, oat byproducts, bakery byproducts, hominy feed, peas, brewers grains, distillers grains, malt sprouts, rice, rice bran, rice flour, other rice byproducts, cereal feed, sucrose, lactose, glucose, dextrose, or maltose, cassava, potatoes, other starchy tubers, or any combination thereof.

33. The method of claim 20 wherein the rumen digestibility of the ruminally digestible starch component is obtained by combining starch ingredients having different ruminal digestibilities.

34. The method of claim 20 wherein the ruminally digestible starch component is processed to be within the ruminally digestible starch component range of either the first feed or the second feed.

35. The method of claim 20 wherein the digestible starch component range of the first feed or the second feed is achieved by including non-fiber carbohydrates, non-structural carbohydrates, soluble carbohydrates, or soluble fiber, or any combination thereof.

36. The method of claim 20 wherein the ruminally digestible starch component comprises:

corn grain, corn silage, corn gluten feed, corn germ meal, corn starch, corn byproducts, sorghum grain, sorghum silage, sorghum byproducts, wheat grain, wheat silage, wheat bran, red dog wheat, wheat germ, wheat flour, wheat middlings, wheat byproducts, barley grain, barley silage, barley byproducts, oat grain, oat silage, oat byproducts, bakery byproducts, hominy feed, peas, brewers grains, distillers grains, malt sprouts, rice, rice bran, rice flour, other rice byproducts, cereal feed, sucrose, lactose, glucose, dextrose, maltose, cassava, potatoes or other starch tubers or any combination thereof.

37. The method of claim 20 wherein the rumen digestibility of the ruminally digestible starch component is obtained by combining starch ingredients having different ruminal digestibilities.

38. The method of claim 20 wherein the ruminally digestible starch component is processed to be within the ruminally digestible starch component range of either the first feed or the second feed.

39. The method of claim 20 wherein the digestible starch component range of the first feed or the second feed is achieved by including non-fiber carbohydrates, non-structural carbohydrates, soluble carbohydrates, or soluble fiber, or any combination thereof.

* * * * *